United States Patent [19]  
Domicone

[11] 4,333,467  
[45] Jun. 8, 1982

[54] NONSTICK CONDUCTIVE COATING

[75] Inventor: Joseph J. Domicone, Horseheads, N.Y.

[73] Assignee: Corning Glass Works, Corning, N.Y.

[21] Appl. No.: 102,887

[22] Filed: Dec. 12, 1979

[51] Int. Cl.$^3$ .............................................. A61B 17/36
[52] U.S. Cl. .......................... 128/303.14; 128/303.17
[58] Field of Search ............... 128/303, DIG. 14, 783, 128/784; 30/140

[56] References Cited

U.S. PATENT DOCUMENTS

| Re. 29,088 | 12/1976 | Shaw | 128/303.17 |
| 3,071,856 | 1/1973 | Fishbein | 128/DIG. 14 |
| 4,161,950 | 7/1979 | Doss et al. | 128/303.14 |
| 4,232,676 | 11/1980 | Herczog | 128/303.14 |
| 4,248,231 | 2/1981 | Herczog et al. | 128/303.14 |

FOREIGN PATENT DOCUMENTS

| 1029363 | 5/1966 | United Kingdom . |
| 1178742 | 1/1970 | United Kingdom . |
| 1247734 | 9/1971 | United Kingdom . |
| 1476121 | 6/1977 | United Kingdom . |

Primary Examiner—Robert W. Michell  
Assistant Examiner—T. J. Wallen  
Attorney, Agent, or Firm—John P. DeLuca

[57] ABSTRACT

An electrically conductive non-stick coating for a substrate for making electrical contact with external materials comprising a layer of conductive material adherently deposited on the substrate and a superposed layer of organic non-stick material on said conductive layer being chemically bonded thereto.

1 Claim, No Drawings

NONSTICK CONDUCTIVE COATING

BACKGROUND OF THE INVENTION

This invention relates to conductive coatings and specifically to a nonstick conductive coating for use with an electrosurgical cutting instrument.

Electrosurgical devices or surgical scalpels, which are adapted to use radio frequency electrical energy in the performance of hemostatic surgery, are disclosed in related commonly owned U.S. Pat. Nos. 4,232,676 to Herczog, and 4,248,231 to Herczog et al. Other such hemostatic surgical instruments are available in the prior art, for example, see U.S. Pat. No. Re. 29,088 for a heated surgical scalpel. There are other variations on the concept of hemostatic surgery including systems utilizing electric discharge to cut and cauterize, and related systems such as shown in U.S. Pat. Nos. 4,161,950, 4,033,351 and 3,913,583.

While the concept involved in the present invention might be adapted for use in many of the aforementioned electrosurgical devices, it is best exemplified for its usefulness in the cutting instruments of the type disclosed by Herczog et al. (hereinafter Herczog or RF blade). In one embodiment, currents are carried to separate electrodes which are desposited near the cutting edge of a glass or glass-ceramic material scalpel or blade. Moisture from incised tissue surfaces completes a circuit from one electrode to the other and the high frequency source generated currents pass through the tissue, generate heat and cause hemostasis in the vicinity of the electrodes.

In such a system it is possible for the blade to stick in the incision, thereby causing apparent dullness of the blade. The problem is alleviated when non-stick coatings are used, however, because of the nature of non-stick materials, many tend to be fragile and are abraded easily. Thus, the non-stick properties degrade in normal use, due in part to actual cutting, and partly due to the frequent wiping necessary in order to remove surgical debris adhered to the blade. When sticking is severe, the blade is unfit for further use and must be discarded. Further, when using the Herczog concept, the non-conductive nature of non-stick films tends to interfere with the conductivity of the electrodes.

There are a number of patents in the prior art disclosing non-stick coatings. These patents mainly relate to the use of fluorocarbon polymers on razor blades for increasing their lubricity and enhancing the comfort of such shaving instruments while in use. Such arrangements are described in U.S. Pat. Nos. 4,012,551 and 3,754,329. There is a copending patent application of R. E. Allen, Ser. No. 102,886, filed this same date and assigned to the assignee herein, disclosing conductive non-stick coatings applied to RF electrosurgical devices.

Allen's patent application teaches that the insulative nature of the non-stick materials normally interferes with the conductivity of the electrodes, but if the material is applied to textured electrodes and subsequently wiped away the surface of the electrode is free to conduct and the instrument exhibits non-stick characteristics. This occurs because the non-stick material permeates microscopic interstices in the electrode surface thereby providing a means for mechanical adherence of one to the other and the wiping step removes sufficient amounts of the insulative non-stick material from high profile points of the electrode surfaces to permit conduction. Allen discloses specific formulations of organic fluorocarbon materials such as those sold by E. I. DuPont de Nemours & Company under the registered trademark TEFLON ®.

The present invention discloses additional useful non-stick materials. While the non-stick coatings hereinafter described, at least partially fill microscopic irregularities or interstices in the conductive material, as in Allen, the materials selected for non-stick properties are believed to exhibit a surface effect or chemical bond with the instrument. The application of the chemically bonded non-stick materials does not require subsequent wiping to effect the required conductivity of the electrodes.

SUMMARY OF THE INVENTION

The invention may be described briefly as an electrically conductive non-stick coating for making electrical contact with electrically conductive external materials comprising, an adherently interconnected mass of conductive material deposited on a substrate and a superposed molecular layer of non-stick material chemically bonded thereover. The conductive material is thus rendered nonstick but remains conductive.

DESCRIPTION OF THE PREFERRED EMBODIMENT

Conductive non-stick electrodes are necessary for the proper operation of a RF-type hemostatic instrument. Non-stick may be defined generally as the condition wherein adhered surgical debris may be readily removed from the instrument by wiping with dry or damp surgical gauze.

The table below lists various materials which were investigated.

TABLE

| Source | Code | Chemical Designation | Type of Bond |
|---|---|---|---|
| Union Carbide | A-1100 | aminopropyl triethoxy-silane | chemical |
| Dow Corning | Z-6040 | glycidoxy propyl tri-methoxysilane (a) | chemical |
| Dow Corning | Z-6030 | methacrylate propyl trimethoxisaline (a) | chemical |
| Dow Corning | DC-200 | silicone fluid (b) | mechanical |
| Dow Corning | DC-1107 | silicone fluid (b) | mechanical |
| Dow Corning | DC-803 | resin (c) | mechanical |
| Dow Corning | DC-804 | resins (c) | mechanical |
| Dow Corning | DC-805 | resin (c) | mechanical |
| Dow Corning | DC2-2300 | lubricant (d) | chemical |
| Dow Corning | FS-1265 | fluorosilicone | mechanical |

(a)-coupling agent
(b)-silicone fluid
DC-200 - $(Me_2SiO)_x$
DC-1107 - $(Me_2SiOH)_x$
(c)-resin
DC-800 series - $(RSiO)$
Where R may be a phenyl, methyl, dimethyl, phenyl-methyl, and trimethyl
(d)-lubricant
DC-2-2300 - (→chemical Name-) appeared to be superior in application and function.

EXAMPLE OF A PREFERRED EMBODIMENT

Prepare a scalpel having a conductive electrode. This may be accomplished by the procedures described in the above mentioned Allen application, but without a non-stick coating. The conductive electrode may be a screen printed silver paste such as Englehardt A3392 fired at about 500°–600° C. The paste is a mixture of silver, organic carriers and glass frit binder. Upon firing, the organics volatilize off while the silver and glass frit sinter and form an adherent conductive coating along the cutting edge of the scalpel. Thereafter prepare a 0.25% solution of 0.5 gms DC-2-2300 lubricant (50% solids in alcohol) by adding 100 gms of tap water. Dip the scalpel into the lubricant solution; rinse with distilled water, follow by a bake at 100°–110° C. for a period of 5–10 minutes.

DC-2-2300 is a water soluble cationic silicone material which, when applied as described above, renders the surface of the scalpel hydrophobic and protectively lubricated. The baked DC-2-2300 coating is permanently bonded to the blade and is non-migrating for durable protection and non-oily characteristics. While the mechanism for adherence is not fully understood, it appears that the DC-2-2300 is a cationic silicone, which has an affinity for anionic glass frit binder materials used for conductive electrodes. As a result, the silicone preferentially seeks out the glass frit and deposits on it through microscopic pinholes in the electrode. A thin film of silicone thus appears to "plate" onto the glass frit material and becomes part of it. This may be referred to as a chemical bond. This type of bond appears to be superior to a mechanical bond because, under normal operating conditions, it can only be removed chemically or by excessive heat. Mechanical type bonds are more readily removed, especially by abrasion.

Some of the chemically bondable materials tested above appear to be coupling agents. That is, the non-stick material molecularly bonds preferentially to the blade at one end of its organosilicone molecule while the other end thereof remains free. The chemically bonded materials appear to attach to the glass frit with a mono-molecular layer thereby allowing conduction therethrough while at the same time exhibiting the desired non-sticking characteristics.

I claim:

1. In an electrosurgical cutting blade for carrying electrical source generated hemostatic and cauterizing currents to a portion of the blade for contacting with tissue, an electrically conductive non-stick electrode deposited near the cutting edge thereof comprising: a first coating of electrically conductive material adherently deposited on said blade, said conductive material having an exposed working surface and intersticies therein producing irregularities in said working surface; a superposed coating of nonstick material adherently deposited and chemically bonded to said first coating in at least said intersticies, to the extent that, the working surface of said first coating is sufficiently conductive through the chemical bonded first coating to carry the hemostatic and cauterizing currents to the tissue and the second coating imparts non-stick characteristics to the blade.

* * * * *